United States Patent
Ki et al.

(10) Patent No.: US 9,554,753 B2
(45) Date of Patent: Jan. 31, 2017

(54) ELECTROCARDIOGRAM (ECG) SENSOR AND METHOD OF OPERATING THE SAME

(71) Applicant: Samsung Electronics Co., Ltd., Suwon-Si, Gyeonggi-Do (KR)

(72) Inventors: Myoung Oh Ki, Seoul (KR); Sang Wook Park, Hwaseong-si (KR); Hee Young Jo, Gwangju-si (KR); Won Hyuk Jung, Yongin-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 32 days.

(21) Appl. No.: 14/590,258

(22) Filed: Jan. 6, 2015

(65) Prior Publication Data

US 2015/0230757 A1    Aug. 20, 2015

(30) Foreign Application Priority Data

Feb. 18, 2014    (KR) ........................ 10-2014-0018377

(51) Int. Cl.
*A61B 5/0402* (2006.01)
*A61B 5/00* (2006.01)
*A61B 5/04* (2006.01)
*A61B 5/0404* (2006.01)

(52) U.S. Cl.
CPC ........... *A61B 5/7214* (2013.01); *A61B 5/0402* (2013.01); *A61B 5/04017* (2013.01); *A61B 5/7246* (2013.01); *A61B 5/0006* (2013.01); *A61B 5/0404* (2013.01)

(58) Field of Classification Search
CPC ... A61B 5/7207; A61B 5/7214; A61B 5/0402; A61B 5/0428; A61B 5/04017
See application file for complete search history.

(56) References Cited

U.S. PATENT DOCUMENTS

| 7,894,885 B2 | 2/2011 | Bartal et al. |
| 8,150,489 B2 | 4/2012 | Thijs et al. |
| 8,515,530 B2 | 8/2013 | Warner et al. |
| 2011/0137200 A1* | 6/2011 | Yin ................... A61B 5/04085 600/547 |
| 2012/0232369 A1 | 9/2012 | Kim et al. |
| 2013/0053675 A1 | 2/2013 | Kim et al. |

(Continued)

FOREIGN PATENT DOCUMENTS

KR    10825888 B1    4/2008

OTHER PUBLICATIONS

B. Ko, "Motrin Artifact Reduction in Electrocardiogram using Adaptive Filtering Based on Half Cell Potential Monitoring", 34th Annual International Conference of the IEEE EMBS, 2012, 4pgs, 978-1-4577-1787-1/12, San Diego, California.

*Primary Examiner* — George Evanisko
(74) *Attorney, Agent, or Firm* — Harness, Dickey & Pierce, P.L.C.

(57) ABSTRACT

An electrocardiogram (ECG) sensor includes a motion artifact detector configured to detect a motion artifact component from a first channel signal of a first channel and a second channel signal of a second channel using a channel offset coefficient. The channel offset coefficient indicates a difference between the first channel signal and the second channel signal. The ECG sensor includes an ECG filter configured to generate an ECG signal by performing a least mean square (LMS) filtering operation on the first channel signal to remove the motion artifact component.

17 Claims, 7 Drawing Sheets

(56) References Cited

U.S. PATENT DOCUMENTS

| | | |
|---|---|---|
| 2013/0116577 A1 | 5/2013 | Yazicioglu et al. |
| 2013/0123652 A1 | 5/2013 | Rubinstein |
| 2013/0190638 A1 | 7/2013 | Chon et al. |
| 2013/0211271 A1 | 8/2013 | Kang et al. |

* cited by examiner

ELECTROCARDIOGRAM (ECG) SENSOR AND METHOD OF OPERATING THE SAME

CROSS-REFERENCE TO RELATED APPLICATIONS

This application claims priority under 35 U.S.C. §119(a) from Korean Patent Application No. 10-2014-0018377 filed on Feb. 18, 2014, the disclosure of which is hereby incorporated by reference in its entirety.

BACKGROUND

At least one example embodiment of the inventive concepts relates to an electrocardiogram (ECG) sensor and/or a method of operating the same, and more particularly, to an ECG sensor for processing a signal for accurate detection of an ECG signal and/or a method of operating the same.

A biopsy system collects and analyzes action current generated in a subject (e.g., a person's heart), electrical changes in the action current, and so on and displays various biometric data of the subject in a form that can be recognized by an examiner. In detail, a biopsy system analyzes the changes in a voltage induced in a measuring electrode attached to a patient, and collects a bio-signal.

To collect a bio-signal using a biopsy system, a measuring electrode needs to be physically attached to the patient's skin. However, it is difficult to detect a signal generated in only the patient because of the patient's continuous motion, poor contact between the measuring electrode and the patient's skin, or an electrical signal generated by the movement of joints or muscles.

Accordingly, an approach for removing noise other than a signal generated in a subject in a biopsy system is desired in order to accurately collect various biometric data in daily life.

SUMMARY

According to at least one example embodiment, an electrocardiogram (ECG) sensor includes a motion artifact detector configured to detect a motion artifact component from a first channel signal of a first channel and a second channel signal of a second channel using a channel offset coefficient. The channel offset coefficient indicates a difference between the first channel signal and the second channel signal. The ECG sensor includes an ECG filter configured to generate an ECG signal by performing a least mean square (LMS) filtering operation on the first channel signal to remove the motion artifact component.

According to at least one example embodiment, the motion artifact detector is configured to detect the motion artifact component by subtracting a signal obtained by dividing the second channel signal by the channel offset coefficient from the first channel signal.

According to at least one example embodiment, the ECG filter is configured to perform the LMS filtering operation by receiving an input signal and a request signal, and outputting an output signal and an error signal. The first channel signal corresponds to the request signal, and the motion artifact component corresponds to the input signal.

According to at least one example embodiment, the ECG filter is configured to generate the output signal by multiplying the input signal by an internal coefficient, generate the error signal by performing subtraction on the request signal and the output signal, and change the internal coefficient to minimize the error signal.

According to at least one example embodiment, the internal coefficient is based on a step coefficient.

According to at least one example embodiment, the ECG sensor includes a correlation calibrator configured to calculate a correlation between the first channel signal and the second channel signal and to compare the calculated correlation with a threshold correlation.

According to at least one example embodiment, the correlation calibrator is configured to generate a signal for requesting to change a position of at least one of the first and second channels if the calculated correlation does not exceed the threshold correlation.

According to at least one example embodiment, a plurality of channels comprising the first channel and the second channel is arranged in a matrix.

According to at least one example embodiment, a method includes detecting a motion artifact component from a first channel signal of a first channel and a second channel signal of a second channel using a channel offset coefficient. The channel offset coefficient indicates a difference between the first channel signal and the second channel signal. The method includes generating an ECG signal by performing a least mean square (LMS) filtering operation on the first channel signal to remove the motion artifact component.

According to at least one example embodiment, the detecting includes subtracting a signal obtained by dividing the second channel signal by the channel offset coefficient from the first channel signal.

According to at least one example embodiment, the LMS filtering operation includes receiving an input signal and a request signal and outputting an output signal and an error signal. The first channel signal corresponds to the request signal, and the motion artifact component corresponds to the input signal.

According to at least one example embodiment, the generating the ECG signal comprises generating the output signal by multiplying the input signal by an internal coefficient, generating the error signal by performing subtraction on the request signal and the output signal, and changing the internal coefficient to minimize the error signal.

According to at least one example embodiment, the internal coefficient is based on a step coefficient.

According to at least one example embodiment, the method includes calculating a correlation between the first channel signal and the second channel signal; and comparing the calculated correlation with a threshold correlation.

According to at least one example embodiment, the method includes changing a position of at least one of the first and second channels if the calculated correlation does not exceed the threshold correlation.

According to at least one example embodiment, an electrocardiogram (ECG) device includes a sensor configured to calculate an offset coefficient based on a first signal from a first channel of a measuring electrode and a second signal from a second channel of the measuring electrode. The calculated offset coefficient indicates a difference between the first signal and the second signal. The sensor is configured to determine an noise component based on the first signal, the second signal, and the calculated offset coefficient. The sensor is configured to perform a filtering operation such that the determined noise component is removed from the first signal.

According to at least one example embodiment, the calculated channel offset coefficient indicates a gain difference between the first and second signals.

According to at least one example embodiment, the filtering operation is a Least Mean Square (LMS) filtering operation.

According to at least one example embodiment, the sensor is configured to determine the noise component by dividing the second channel by the coefficient and subtracting a result of the dividing from the first signal.

According to at least one example embodiment, the sensor is configured to calculate a correlation between the first signal and the second signal, and output a request to change a position of the at least one of the first channel and the second channel based on whether the calculated correlation exceeds a threshold.

BRIEF DESCRIPTION OF THE DRAWINGS

The above and other features and advantages of the inventive concepts will become more apparent by describing in detail example embodiments thereof with reference to the attached drawings in which.

DETAILED DESCRIPTION OF EXAMPLE EMBODIMENTS

Inventive concepts will now be described more fully with reference to the accompanying drawings, in which example embodiments of are shown. These example embodiments are provided so that this disclosure will be thorough and complete, and will fully convey inventive concepts of to those skilled in the art. Inventive concepts may be embodied in many different forms with a variety of modifications, and a few embodiments will be illustrated in drawings and explained in detail. However, this should not be construed as being limited to example embodiments set forth herein, and rather, it should be understood that changes may be made in these example embodiments without departing from the principles and spirit of inventive concepts, the scope of which are defined in the claims and their equivalents. Like numbers refer to like elements throughout. In the drawings, the thicknesses of layers and regions are exaggerated for clarity.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Specific details are provided in the following description to provide a thorough understanding of example embodiments. However, it will be understood by one of ordinary skill in the art that example embodiments may be practiced without these specific details. For example, systems may be shown in block diagrams so as not to obscure example embodiments in unnecessary detail. In other instances, well-known processes, structures and techniques may be shown without unnecessary detail in order to avoid obscuring example embodiments.

In the following description, illustrative embodiments will be described with reference to acts and symbolic representations of operations (e.g., in the form of flow charts, flow diagrams, data flow diagrams, structure diagrams, block diagrams, etc.) that may be implemented as program modules or functional processes include routines, programs, objects, components, data structures, etc., that perform particular tasks or implement particular abstract data types and may be implemented using existing hardware in existing electronic systems (e.g., electronic imaging systems, image processing systems, digital point-and-shoot cameras, personal digital assistants (PDAs), smartphones, tablet personal computers (PCs), laptop computers, etc.). Such existing hardware may include one or more Central Processing Units (CPUs), digital signal processors (DSPs), application-specific-integrated-circuits (ASICs), field programmable gate arrays (FPGAs) computers or the like.

Although a flow chart may describe the operations as a sequential process, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible or non-transitory machine readable mediums for storing information. The term "computer-readable medium" may include, but is not limited to, portable or fixed storage devices, optical storage devices, and various other tangible or non-transitory mediums capable of storing, containing or carrying instruction(s) and/or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, a processor or processors may be programmed to perform the necessary tasks, thereby being transformed into special purpose processor(s) or computer(s).

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "includes", "including", "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which inventive concepts belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "and/or" includes any and all combinations of one or more of the associated listed items. Expressions such as "at least one of," when preceding a list of elements, modify the entire list of elements and do not modify the individual elements of the list.

Figure 1:
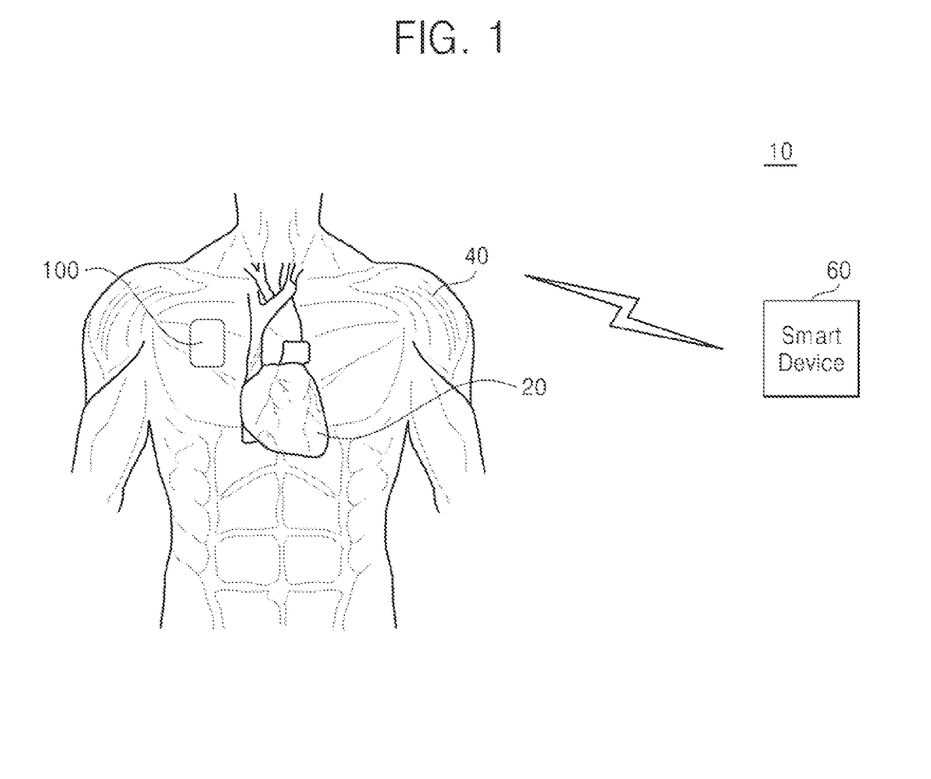
FIG. 1 is a schematic diagram of an electrocardiogram (ECG) sensing system according to at least one example embodiment of the inventive concepts.

FIG. 1 is a schematic diagram of an electrocardiogram (ECG) sensing system 10 according to at least one example embodiment of the inventive concepts. The ECG sensing system 10 is an example of a biopsy system. It senses and analyzes an ECG signal generated by a cardiac action (i.e., a potential change generated by depolarization and repolarization). The ECG sensing system 10 may include a smart device 60 and an ECG sensor 100.

The smart device 60 may be a device, such as an ECG tester, a smartphone, a wearable device like a wearable robot, smart goggles, or a smart watch, a smart television (TV), a notebook, a navigator, etc. which communicates with the ECG sensor 100 via a wired and/or wireless connection. The smart device 60 may store and analyze an ECG signal received from the ECG sensor 100 and output the ECG signal in a form of image or voice so that a user can recognize the output. In other words, the user is able to check the state of the heart of a person to which the ECG sensor 100 is attached from information output from the smart device 60.

The smart device 60 may output an image or voice allowing a user to recognize that it is desired to adjust the attached position of the ECG sensor 100 according to a position adjustment signal received from the ECG sensor 100 or to recognize the smart device's 60 decision(s) on an ECG signal received from the ECG sensor 100. The smart device 60 may transmit a control signal for controlling the ECG sensor 100 (e.g., the operation of a control unit 150 in FIG. 2) to the ECG sensor 100.

The ECG sensor 100 may be attached to the skin of a person's body part (e.g., chest, abdomen, back, arm, or leg). The ECG sensor 100 may detect an ECG signal generated in the person's heart 20 and transmit the ECG signal to the smart device 60. The ECG sensor 100 receives not only the ECG signal generated in the heart 20 but also noise generated by motion artifacts.

The sources of motion artifacts may be categorized into three types. The first type may be the change in impedance between an electrode (e.g., an electrode included in each of channels C11 through C44 in FIG. 2), which contacts a person's skin in the ECG sensor 100, and the skin. The second type may be a half-cell potential occurring due to the substance difference between the electrode and the skin. The third type may be a bio-signal generated in a body part other than the heart 20. For instance, an electromyogram (EMG) signal may be generated by the movement of an arm muscle 40 illustrated in FIG. 1 and may flow in the ECG sensor 10 together with an ECG signal.

When an ECG signal is analyzed, figures such as a peak value and a slope of the ECG signal over time are important. Motion artifacts change these figures, and therefore, it is important to effectively mitigate (or alternatively, remove) the motion artifacts caused by the sources of motion artifacts.

Figure 2:
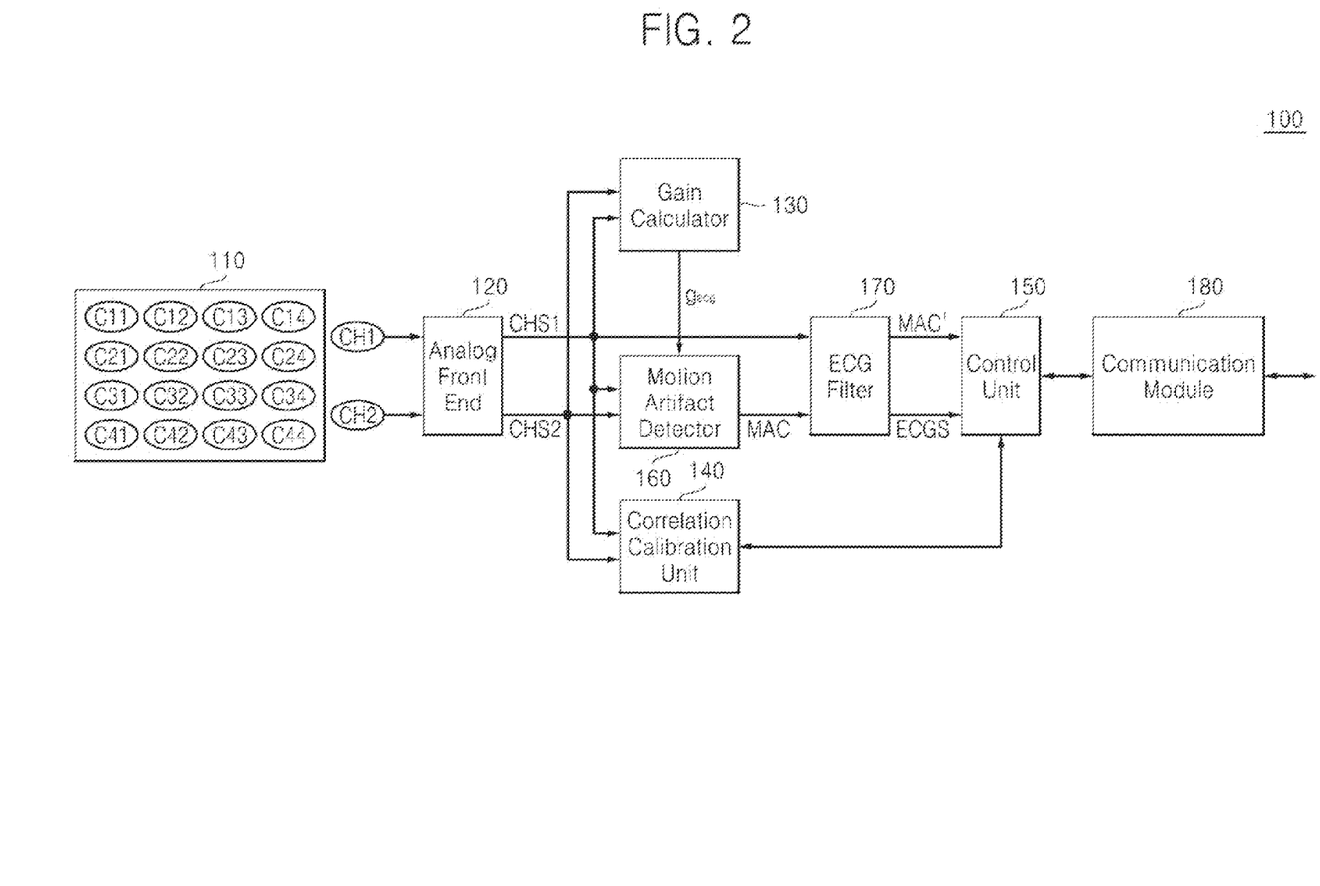
FIG. 2 is a detailed block diagram of an ECG sensor illustrated in FIG. 1.
Figure 3:
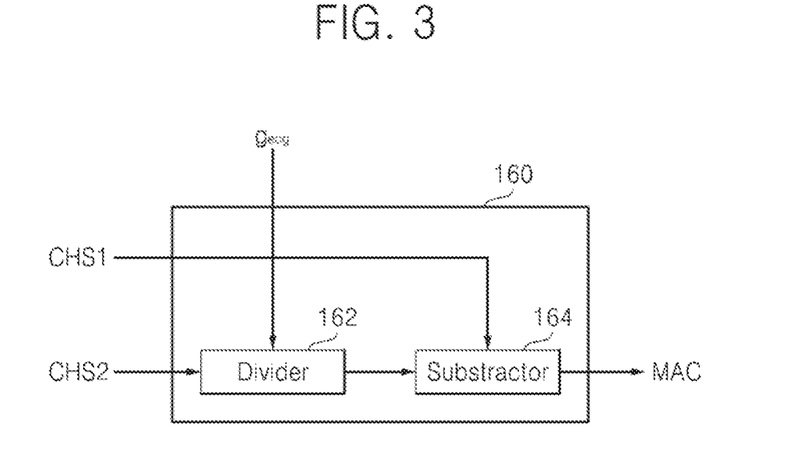
FIG. 3 is a detailed block diagram of a motion artifact detector illustrated in FIG. 2.
Figure 4:
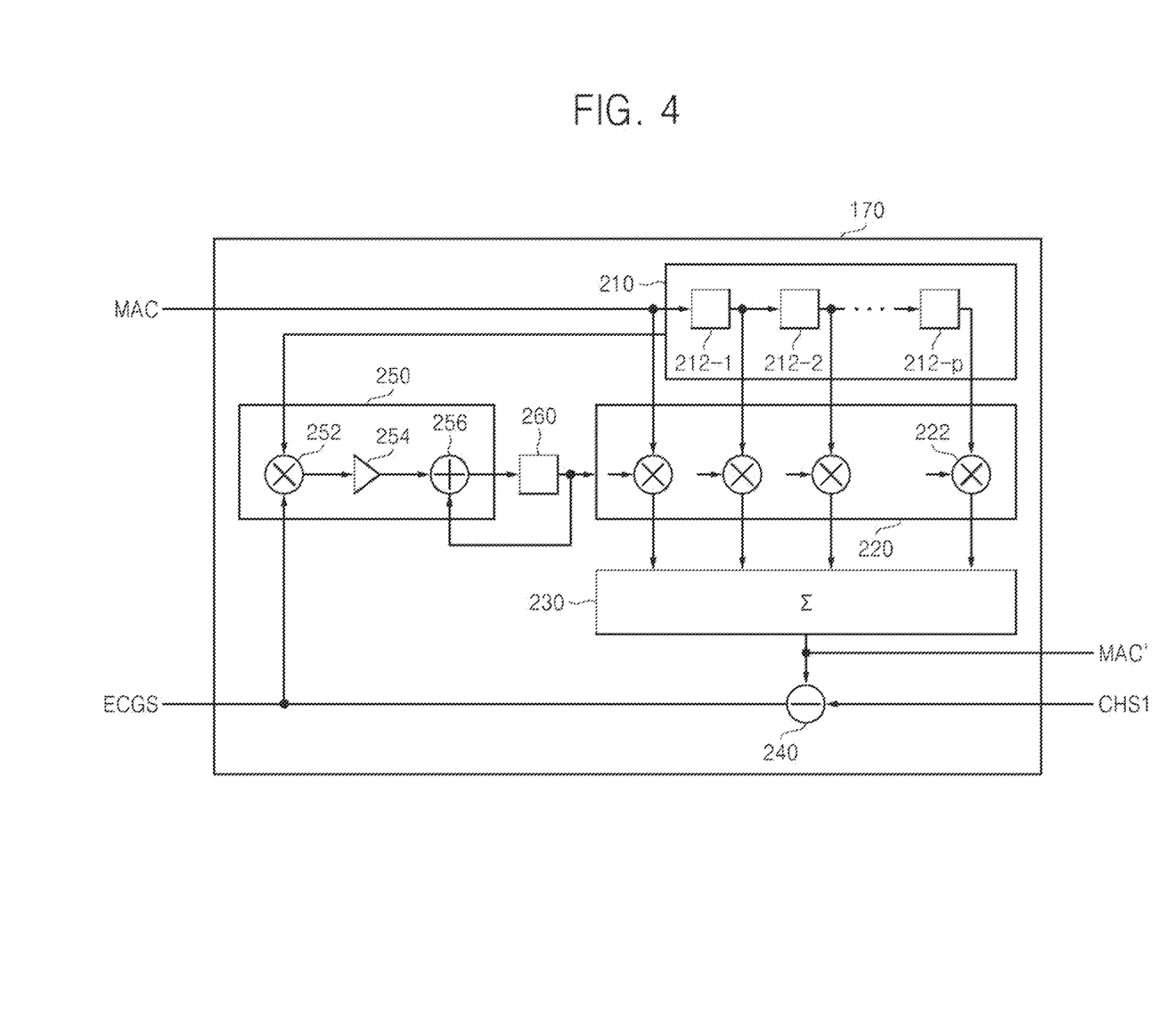
FIG. 4 is a detailed block diagram of an ECG filter illustrated in FIG. 2.
Figure 5:
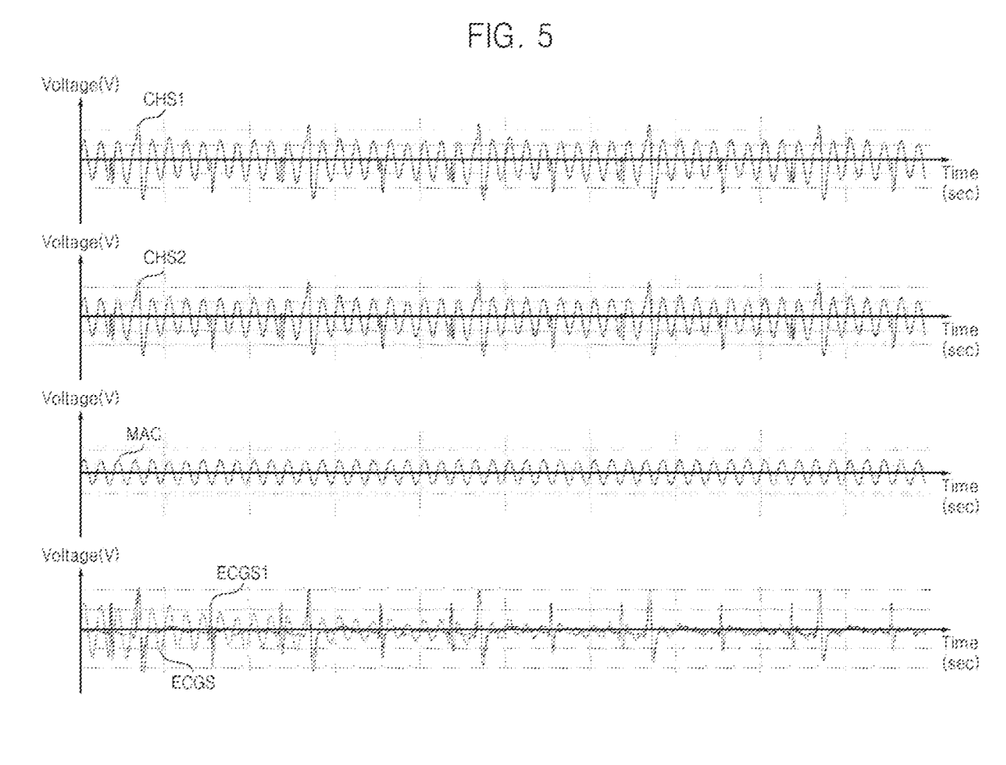
FIG. 5 is a timing chart of signals in the operation of the ECG sensor.

FIG. 2 is a detailed block diagram of the ECG sensor 100 illustrated in FIG. 1. FIG. 3 is a detailed block diagram of a motion artifact detector 160 illustrated in FIG. 2. FIG. 4 is a detailed block diagram of an ECG filter 170 illustrated in FIG. 2. FIG. 5 is a timing chart of signals in the operation of the ECG sensor 100.

Referring to FIGS. 1 through 5, the ECG sensor 100 may include an electrode unit 110 (or measuring electrode), an analog front end 120, a gain calculator 130, a correlation calibration unit 140 (or correlation calibrator), a control unit (or controller) 150, the motion artifact detector 160, the ECG filter 170, and a communication module 180. The ECG sensor 100 may be implemented in the form of a patch that can be attached to human skin.

The electrode unit 110 may include at least two channels. The electrode unit 110 may directly contact human skin and transmit a signal. For instance, as shown in FIG. 2, the electrode unit 110 may include a plurality of channels C11 through C44 arranged in a matrix of four rows and four columns. The electrode unit 110 has the matrix form of four rows and four columns in an example embodiment illustrated in FIG. 2, but the inventive concepts are not restricted thereto. When the electrode unit 110 includes a plurality of the channels C11 through C44, the position of one of the channels may change without changing the position of the electrode unit 110 on the skin.

Each of the channels C11 through C44 may include a positive electrode and a negative electrode, which contact human skin and receive a bio-signal, and a ground electrode that provides a reference potential. The ground electrode may be shared by the channels C11 through C44.

Two channels among the channels C11 through C44 may be a first channel CH1 and a second channel CH2, which may be selected by the control unit 150. A channel selected as the first channel CH1 and a channel selected as the second channel CH2 may transmit an analog bio-signal to the analog front end (or analog front end device) 120.

The analog front end 120 may receive bio-signals respectively from the first and second channels CH1 and CH2 and may generate a first channel signal CHS1 and a second channel signal CHS2 in a digital form. The analog front end 120 may include an amplifier (not shown) that amplifies a bio-signal and an analog-to-digital converter (ADC) (not shown) that converts an amplified analog signal to a digital signal.

The first channel signal CHS1 and the second channel signal CHS2 illustrated in FIG. 5 may include an ECG signal generated in human heart and a motion artifact signal generated by motion artifacts. In other words, the first channel signal CHS1 may be represented with the sum of an ECG signal, i.e., $ecg_1(n)$, and a motion artifact signal, i.e., $ma_1(n)$ and the second channel signal CHS2 may be represented with the sum of an ECG signal, i.e., $ecg_2(n)$, and a motion artifact signal, i.e., $ma_2(n)$. Here, $ma_1(n)$ and the $ma_2(n)$ may include any other noise as well as a signal caused by motion artifacts. The mark "(n)" indicates that the value has been digitized by the analog front end 120.

Although $ecg_1(n)$ and $ecg_2(n)$ are signals generated in the heart of one person, they are received through different channels CH1 and CH2 at different positions and may have different phases and/or waveforms. In the context of this application, a channel offset coefficient may indicate a difference between signals $ecg_1(n)$ and $ecg_2(n)$, For example, when determining whether a correlation exceeds a threshold correlation, it is assumed that there is no phase difference and no waveform difference between $ecg_1(n)$ and $ecg_2(n)$, but that there is a gain difference according to a channel offset coefficient, i.e., $g_{ecg}$. Therefore, a relation of $ecg_2(n)=ecg_1(n)*g_{ecg}$ is formed. Similarly, a relation of $ma_2(n)=ma_1(n)*g_{ma}$ is formed between $ma_1(n)$ and $ma_2(n)$ according to a channel offset coefficient, i.e., $g_{ma}$, under the above-described assumption. The correlation and threshold correlation is explained in more detail below with reference to correlation calibration unit 140.

The gain calculator 130 may calculate a channel offset coefficient, $g_{ecg}$, which is the gain difference between an ECG signal, $ecg_1(n)$, in the first channel signal CHS1 and an ECG signal, $ecg_2(n)$, in the second channel signal CHS2 according to the control of the control unit 150. The control unit 150 may control the gain calculator 130 to calculate the channel offset coefficient, $g_{ecg}$, when the control unit 150 determines that the generation of a motion artifact signal has been suppressed based on a request from the smart device 60 or the control unit's 150 own decision using an acceleration sensor (not shown) indicating that a person, i.e., a patient is not moving.

In addition, the control unit 150 may control the gain calculator 130 to calculate the channel offset coefficient, $g_{ecg}$, when the correlation between the first channel signal CHS1 and the second channel signal CHS2 exceeds the threshold correlation in order to stop an undesired operation. The channel offset coefficient, $g_{ecg}$, may be maintained until there is special control of the control unit 150. In this case, since the first channel signal CHS1 and the second channel signal CHS2 include only an ECG signal, the gain calculator 130 may calculate the channel offset coefficient, $g_{ecg}$, by dividing the second channel signal CHS2, $ecg_2(n)$, by the first channel signal CHS1, $ecg_1(n)$, and may provide $g_{ecg}$ for the motion artifact detector 160.

The correlation calibration unit 140 may calculate the correlation between the first channel signal CHS1 and the second channel signal CHS2 and compare the correlation with a desired (or alternatively, predetermined) threshold correlation according to the control of the control unit 150.

The correlation calibration unit 140 may provide the comparison result for the control unit 150. The correlation calibration unit 140 may newly calculate the correlation between the first channel signal CHS1 and the second channel signal CHS2 when the position of the electrode unit 110 is changed, when the position of at least one of the first and second channels CH1 and CH2 is changed, when there is a request (e.g., a software algorithm for periodic calibration) from the control unit 150, or when there is a request from the smart device 60.

When the correlation does not exceed the threshold correlation, the correlation calibration unit 140 may request the control unit 150 to change the position of the electrode unit 110 or change the position of at least one of the first and second channels CH1 and CH2. When the position of the electrode unit 110 is requested to be changed, the control unit 150 may transmit a position adjustment signal to the smart device 60 through the communication module 180 to request the position change. When the position of least one of the first and second channels CH1 and CH2 is requested to be changed, the control unit 150 may control the connection between the electrode unit 110 and the analog front end 120 to change the position of the least one of the first and second channels CH1 and CH2.

In at least one example embodiment, when the correlation does not exceed the threshold correlation and even though the position of the least one of the first and second channels CH1 and CH2 is continuously changed, the control unit 150 may request the change of the position of the electrode unit 110.

When the correlation exceeds the threshold correlation, the control unit 150 may control the gain calculator 130 to calculate a channel offset coefficient, $g_{ecg}$, according to the comparison result of the correlation calibration unit 140. The control unit 150 may control the overall operation of the elements 110, 120, 130, 140, 160, 170, and 180 of the ECG sensor 100. The control unit 150 may control the elements 130, 160, and 170 to operate when the correlation exceeds the threshold correlation.

The motion artifact detector 160 may detect a motion artifact component (or noise component) MAC in the first and second channel signals CHS1 and CHS2 using the channel offset coefficient, $g_{ecg}$, provided by the gain calculator 130. Referring to FIG. 3, the motion artifact detector 160 may include a divider 162 and a subtractor 164.

The divider 162 may divide the second channel signal CHS2 by the channel offset coefficient, $g_{ecg}$. In other words, since the second channel signal CHS2 is $ecg_2(n)+ma_2(n) =ecg_1(n)*g_{ecg}+ma_1(n)*g_{ma}$, an output of the divider 162 is $ecg_1(n)+ma_1(n)*g_{ma}/g_{ecg}$.

The subtractor 164 may subtract the first channel signal CHS1 from the output of the divider 162. In other words, since the first channel signal CHS1 is $ecg_1(n)+ma_1(n)$, an output of the subtractor 164, i.e., the motion artifact component MAC is $\{ecg_1(n)+ma_1(n)\}-\{ecg_1(n)+ma_1(n)*g_{ma}/g_{ecg}\}=(1-g_{ma}/g_{ecg})*ma_1(n)=k*ma_1(n)$. Therefore, the motion artifact detector 160 may generate the motion artifact component MAC having a value of $k*ma_1(n)$ related with only a motion artifact signal. The motion artifact component MAC illustrated in FIG. 5 may have any amplitude and cycle over time.

The ECG filter 170 may have the first channel signal CHS1 and the motion artifact component MAC as inputs and perform a filter operation (e.g., a least mean square (LMS) filtering operation), thereby generating an ECG signal ECGS corresponding to a result of removing the motion artifact signal, $ma_1(n)$, from the first channel signal CHS1.

The LMS filtering is an example of adaptive filtering and the ECG filter 170 is a non-linear filter of which the coefficient value is updated according to an input signal.

The LMS filtering performed by the ECG filter 170 may be an operation of receiving an input signal and a request signal and outputting an error signal and an output signal. The ECG filter 170 may include an input vector block 210, a vector operation block 220, an output signal generator 230, an error signal generator 240, an internal coefficient generator 250, and an internal coefficient storage block 260.

The input vector block 210 may include "p" registers 212-1 through 212-$p$ (where "p" is an integer of at least 1) that sequentially store a digital motion artifact component MAC corresponding to an input signal. For instance, when first through third motion artifact components MAC are sequentially input to the input vector block 210, the register 212-1 at the left most side may store the first through third motion artifact components MAC in first through third periods, respectively, and then sequentially shift them to the following register 212-2. The period may be the period of a clock signal (not shown) used for operating the ECG filter 170.

The vector operation block 220 may receive an internal coefficient w(n−1) (i.e., a vector comprised of p+1 digital values) from the internal coefficient storage block 260 and may perform multiplication on the vector and an input signal stored in each of the "p" registers 212-1 through 212-$p$ and multiplication on the vector and an input signal currently received in a present period. The multiplications may be performed using the "p" registers 212-1 through 212-$p$ and "p+1" first multipliers 222 corresponding to a current input signal.

The output signal generator 230 may generate a changed motion artifact component MAC' as an output signal by adding the multiplication results, i.e., the outputs of the vector operation block 220. The error signal generator 240 may generate an error signal by subtracting the output signal from the first channel signal CHS1. Here, the first channel signal CHS1 may be to a request signal. The error signal may correspond to the ECG signal ECGS. In particular, when the ECG filter 170 reaches the steady state, the ECG signal ECGS becomes very close to a pure ECG signal obtained as a result of removing a motion artifact signal from the first channel signal CHS1.

The internal coefficient generator 250 may include a second multiplier 252 that performs multiplication on the error signal ECGS and an input signal from input block 210 using a weight of a step coefficient. The internal coefficient generator 250 may also include an inverter 254 that inverts the sign of an output of the second multiplier 252, and an adder 256 that adds a value stored in the internal coefficient storage block 260 and an output of the inverter 254. In other words, the internal coefficient generator 250 may perform multiplication on the step coefficient, the ECG signal ECGS, and the motion artifact component MAC, invert the sign of the multiplication result, and then add a previous internal coefficient of w(n−1) to the multiplication result, thereby generating a new internal coefficient of w(n). At this time, the second multiplier 252 may receive a vector input signal composed of "p+1" digital values, i.e., values from the "p" registers 212-1 through 212-$p$ in the input vector block 210, and a new input signal currently input in a present period and may perform operations on the vector input signal.

The internal coefficient storage block 260 may store a current internal coefficient of w(n) in synchronization with a first period of a clock signal (not shown) and then may output the internal coefficient w(n) as a previous internal coefficient of w(n−1) in a following period of the clock signal.

The LMS filtering performed by the ECG filter 170 will be described using equations, in which the input signal, the request signal, the output signal, and the error signal are represented with u(n), d(n), y(n), and e(n), respectively. The input signal and the request signal correspond to the motion artifact component MAC and the first channel signal CHS1, respectively. The output signal and the error signal may correspond to the changed motion artifact component MAC' and the ECGS signal, respectively. Bold letters in Equations 1 through 3 indicate vectors.

The internal coefficient of w(n) may be defined as Equation 1:

$$w(n)=w(n-1)-\mu \cdot e(n) \cdot u(n). \qquad (1)$$

The vector, w(n), may be expressed as a result of subtracting a result of multiplication of a step coefficient pi, error signal of e(n), and vector input signal of u(n) from the vector, w(n−1), according to the operation of the internal coefficient generator 250. Here, w(n−1) is an internal coefficient in a previous period and w(n) is an internal coefficient in a current period, but w(n−1) may be used when the output signal and the error signal are calculated in the current period. The vector input signal, u(n), is a vector expression of digital values respectively stored in the registers 212-1 through 212-$p$ and a new input signal in the current period.

At this time, the vector, w(n−1), includes "p+1" digital values. When the vector, w(n), is expressed in a matrix of "p+1" columns (i.e., first through (p+1)-th columns) and one row, the vector input signal, u(n), may also be expressed in a matrix of "p+1" columns (i.e., first through (p+1)-th columns) and one row. Accordingly, the first through (p+1)-th columns in the vector, w(n), correspond to the first through (p+1)-th columns in the vector input signal, u(n), respectively, in operations. For instance, in the operations of the adder 256 and the first multipliers 222, an operation may be performed on an input signal stored in the leftmost register 212-1 and a value at the second column in the vector, w(n−1), and an operation may be performed on a current input signal in the present period and a value at the first column in the vector, w(n−1).

As shown in Equation 1, w(n) is determined by a step coefficient "μ", where the step coefficient "μ" determines a rate at which the ECG filter 170 reaches the steady state and an error in the steady state. In at least one example embodiment, the step coefficient "μ" may be adjusted by the control unit 150 and a relatively high step coefficient may be used until the ECG filter 170 reaches the steady state and a relatively low step coefficient may be used after the ECG filter 170 reaches the steady state. The step coefficient "p." may be user defined and/or based on empirical evidence.

The output signal, y(n), may be expressed as Equation 2:

$$y(n)=w(n-1)\cdot u(n)=w(n-1)\cdot k \cdot ma_1(n) \qquad (2)$$

In other words, the output signal, y(n), may be expressed as the product of the vector, w(n−1), and the vector input signal, u(n), according to the operation of the vector operation block 220. The vector input signal, u(n), corresponds to the motion artifact components MAC which are subsequently stored, and therefore, the output signal, y(n), may be expressed as the product of the vector of w(n−1), a constant k, and a vector motion artifact signal $ma_1(n)$. The constant k may be user defined and/or based on empirical evidence.

The error signal, e(n), may be expressed as Equation 3:

$$e(n) = d(n) - y(n) \quad (3)$$
$$= \{ecg_1(n) + ma_1(n)\} - \{w(n-1) \cdot k \cdot ma_1(n)\}$$
$$= ecg_1(n) + \{ma_1(n) - w(n-1) \cdot k \cdot ma_1(n)\}$$
$$= ecg_1(n) + \{(1 - w(n-1) \cdot k) \cdot ma_1(n)\}$$

The error signal, e(n), is a result of subtracting the output signal, y(n), from the request signal, d(n), according to the operation of the error signal generator 240. Since, the request signal, d(n), and the output signal, y(n), correspond to the first channel signal CHS1 and y(n) expressed as Equation 2, respectively, the error signal, e(n), may be put into Equation 3.

In other words, the error signal, e(n), is a value obtained by adding the ECG signal, $ecg_1(n)$, in the first channel signal CHS1 and the product of the motion artifact signal $ma_1(n)$ in the first channel signal CHS1 and a variable of (1−w(n−1)·k) adjusted by the ECG filter 170. The ECG filter 170 performs the LMS filtering, which is a process of changing an internal coefficient to minimize the error signal, e(n). In addition, since the ECG signal, $ecg_1(n)$, and the motion artifact signal $ma_1(n)$ are statistically independent from each other, (that is, their causes of occurrence are not related with and do not influence each other), the ECG filter 170 causes the adjustable variable of (1−w(n−1)·k) to converge to "0" in order to minimize the error signal, e(n), through the LMS filtering.

The control unit 150 may calculate how close the variable of (1−w(n−1)·k) becomes to "0" using a special logic (not shown) and may determine that the ECG filter 170 has reached the steady state when the variable of (1−w(n−1)·k) is in a desired (or alternatively, predetermined) range. In other words, when the ECG filter 170 reaches the steady state, the error signal, e(n), i.e., the ECG signal ECGS may be considered as the ECG signal, $ecg_1(n)$, corresponding to the first channel signal CHS1 from which components related with motion artifacts have been removed.

FIG. 5 shows the ECG signal ECGS corresponding to the first channel signal CHS1 from which a motion artifact signal has been removed by the ECG filter 170. The ECG signal ECGS appearing right after the operation of the ECG filter 170 starts has a different waveform than an ECG signal ECGS1 in the first channel signal CHS1, but the ECG signal ECGS appearing a desired (or alternatively, predetermined) period of time after has nearly the same waveform as the ECG signal ECGS1 in the first channel signal CHS1. The desired (or alternatively, predetermined) period of time and the waveform similarity may vary with the step coefficient "μ". In other words, as the step coefficient "g" increases, the waveforms may become nearly the same in a short time, but the waveform similarity may be low. Therefore, the step coefficient "μ" may be adjusted on the basis of the steady state.

Example embodiments of the inventive concepts have been described on an assumption that an ECG signal in the first channel signal CHS1 is an ECG signal generated in a human heart, but design change is possible on an assumption that the second channel signal CHS2 is an ECG signal generated in the human heart. In addition, the ECG signal ECGS may be subjected to signal processing such as level conversion in the communication module 180 and then transmitted to the smart device 60.

In the steady state, the output signal, y(n), may be expressed as Equation 4:

$$y(n) = d(n) - e(n) \quad (4)$$
$$= \{ecg_1(n) + ma_1(n)\} - ecg_1(n)$$
$$= ma_1(n)$$

In the steady state, the error signal, e(n), corresponds to the ECG signal, $ecg_1(n)$, in the first channel signal CHS1, and therefore, the output signal, y(n), corresponds to the motion artifact signal $ma_1$ (n) in the first channel signal CHS1. The communication module 180 may transmit the ECG signal ECGS to the smart device 60 via a wired and/or wireless connection. The communication module 180 may also mediate control signals between the communication module 180 and the smart device 60.

Each of the elements 110, 120, 130, 140, 150, 160, 170, and 180 of the ECG sensor 100 may be implemented in software, hardware, or a combination thereof and it may be partially or entirely implemented in a single chip. According to at least one example embodiment of the inventive concepts, the ECG sensor 100 efficiently removes various noises other than an ECG signal generated in a human heart.

Figure 6:
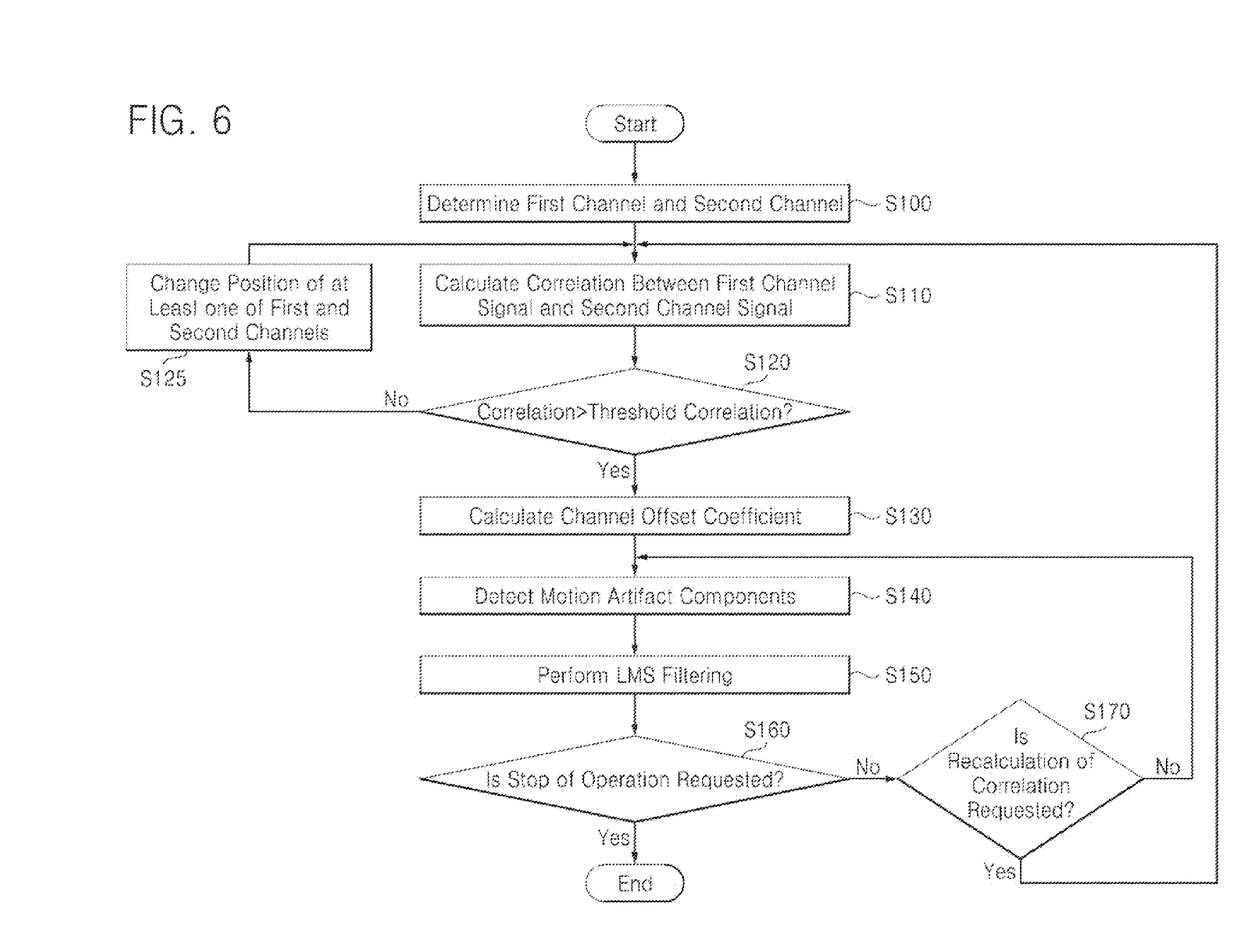
FIG. 6 is a flowchart of a method of operating the ECG sensor illustrated in FIG. 2 according to at least one example embodiment of the inventive concepts.
Figure 7:
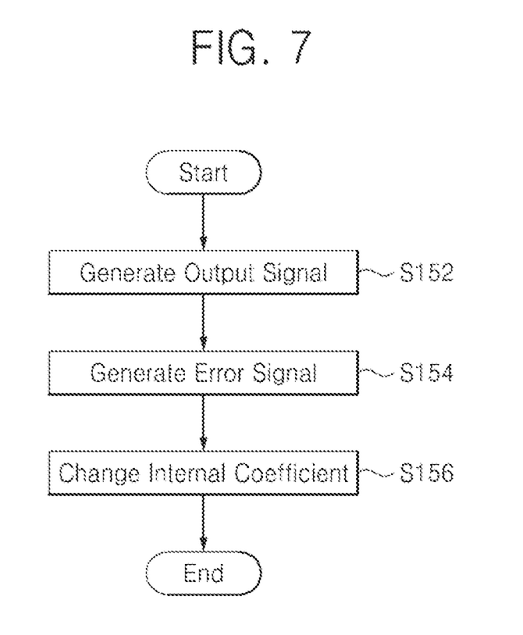
FIG. 7 is a flowchart for explaining the operation of a least mean square (LMS) filter illustrated in FIG. 6.

FIG. 6 is a flowchart of a method of operating the ECG sensor 100 illustrated in FIG. 2 according to at least one example embodiment of the inventive concepts. FIG. 7 is a flowchart for explaining the operation of an LMS filter illustrated in FIG. 6.

Referring to FIGS. 1 through 7, in operation S100, the ECG sensor 100 may determine a position at which the ECG sensor 100 (or the electrode unit 110) is attached and the first channel CH1 and the second channel CH2 from among the channels C11 through C44. In operation S110, the correlation calibration unit 140 may calculate a correlation between the first channel signal CHS1 and the second channel signal CHS2 according to the control of the control unit 150. In operation S120, the correlation calibration unit 140 may compare the correlation with a desired (or alternatively, predetermined) threshold correlation.

In operation S125, when the correlation does not exceed the threshold correlation (i.e., in case of NO in operation S120), the correlation calibration unit 140 may request the control unit 150 to change the position of the electrode unit 110 or the position of at least one of the first and second channels CH1 and CH2 so that the position of the at least one of the first and second channels CH1 and CH2 is changed. The correlation calibration unit 140 may newly calculate a correlation between the first channel signal CHS1 and the second channel signal CHS2 when the position of the electrode unit 110 is changed, when the position of the at least one of the first and second channels CH1 and CH2 is changed, when there is a request of the control unit 150 (e.g., a software algorithm periodically executing calibration), or when there is a request from the smart device 60.

In operation S130, when the correlation exceeds the threshold correlation (i.e., in case of YES in operation S120), the gain calculator 130 may calculate the channel offset coefficient, $g_{ecg}$, i.e., the gain difference between an ECG signal, $ecg_1(n)$, in the first channel signal CHS1 and an ECG signal, $ecg_2(n)$, in the second channel signal CHS2 according to the control of the control unit 150. In operation S140, the motion artifact detector 160 may detect the motion artifact component MAC in the first and second channel signals CHS1 and CHS2 using the channel offset coefficient, $g_{ecg}$, received from the gain calculator 130.

In operation S150, the ECG filter 170 may perform LMS filtering on the first channel signal CHS1 and the motion artifact component MAC, thereby generating the ECG signal ECGS corresponding to the first channel signal CHS1 from which the motion artifact signal $ma_1(n)$ has been removed. In operation 5150, the input vector block 210 may sequentially store digital motion artifact components MAC corresponding to input signals. The vector operation block 220 receives an internal coefficient of w(n−1) from the internal coefficient storage block 260 and multiplies the internal coefficient of w(n−1) by the motion artifact components MAC. The output signal generator 230 may add the multiplication results received from the vector operation block 220 and generate the changed motion artifact component MAC'. Thus, as shown in FIG. 7, the ECG filter 170 may output the changed motion artifact component MAC' as an output signal in operation S152.

Still referring to FIG. 7, in operation S154, the error signal generator 240 may generate the ECG signal ECGS corresponding to an error signal by subtracting the changed motion artifact component MAC' from the first channel signal CHS1, where the first channel signal CHS1 corresponds to a request signal. The internal coefficient generator 250 may perform multiplication on the error signal and the input signal using a weight of the step coefficient, invert the sign of an output of the second multiplier 252, and add a value stored in the internal coefficient storage block 260 and an output of the inverter 254. Thus, in operation S156, the ECG filter 170 may generate the internal coefficient of w(n−1).

Referring back to FIG. 6, the control unit 150 may stop the operation of the ECG sensor 100 when there is a request to stop the operation of the ECG sensor 100 from the smart device 60 (i.e., in case of YES in operation S160). In operation S170, when there is no request to stop the operation of the ECG sensor 100 from the smart device 60 (i.e., in case of NO in operation S160), the control unit 150 may determine whether there is a request to newly calculate the correlation between the first channel signal CHS1 and the second channel signal CHS2. When there is no request to newly calculate the correlation (i.e., in case of NO in operation S170), the method goes to operation S140. When there is any request to newly calculate a correlation (i.e., in case of YES in operation S170), the correlation calibration unit 140 may newly calculate the correlation between the first channel signal CHS1 and the second channel signal CHS2 according to the control of the control unit 150 in operation S110. The correlation recalculation request may be generated when a result of analyzing the ECG signal ECGS is not satisfactory.

As described above, according to at least one example embodiment of the inventive concepts, an ECG sensor efficiently removes various noises other than an ECG signal generated in a patient.

While the inventive concepts have been particularly shown and described with reference to example embodiments thereof, it will be understood by those of ordinary skill in the art that various changes in forms and details may be made therein without departing from the spirit and scope of the inventive concepts as defined by the following claims.

What is claimed is:

1. An electrocardiogram (ECG) sensor comprising:
   a motion artifact detector configured to receive a channel offset coefficient, a first channel signal of a first channel, and a second channel signal of a second channel, and detect a motion artifact component from the first channel signal of the first channel and the second channel signal of the second channel based on the channel offset coefficient, the channel offset coefficient indicating a difference between the first channel signal and the second channel signal; and
   an ECG filter configured to receive the motion artifact component and generate an ECG signal by performing a least mean square (LMS) filtering operation on the first channel signal to remove the motion artifact component,
   wherein the motion artifact detector is configured to detect the motion artifact component by subtracting from the first channel signal a signal obtained by dividing the second channel signal by the channel offset coefficient.

2. The ECG sensor of claim 1, wherein the ECG filter is configured to perform the LMS filtering operation by receiving an input signal and a request signal, and outputting an output signal and an error signal, the first channel signal corresponding to the request signal, and the motion artifact component corresponding to the input signal.

3. The ECG sensor of claim 2, wherein
   the ECG filter is further configured to
      generate an internal coefficient by multiplying the error signal and the input signal,
      generate the output signal by multiplying the input signal by the internal coefficient,
      generate the error signal by performing subtraction on the request signal and the output signal, and
      change the internal coefficient to minimize the error signal.

4. The ECG sensor of claim 3, wherein the internal coefficient is based on a step coefficient, the step coefficient indicating a rate at which the ECG filter reaches a steady state and an error in the steady state, the step coefficient adjusted by a controller.

5. The ECG sensor of claim 1, further comprising:
   a correlation calibrator connected to the motion artifact detector and configured to calculate a correlation between the first channel signal and the second channel signal and compare the calculated correlation with a threshold correlation.

6. The ECG sensor of claim 5, wherein the correlation calibrator is configured to generate a signal for requesting to change a position of at least one of the first and second channels if the calculated correlation does not exceed the threshold correlation.

7. The ECG sensor of claim 1, further comprising: a plurality of channels including the first channel and the second channel, wherein the plurality of channels arranged in a matrix.

8. A method of operating an electrocardiogram (ECG) sensor, the method comprising:
   detecting a motion artifact component from a first channel signal of a first channel and a second channel signal of a second channel using a channel offset coefficient, the channel offset coefficient indicating a difference between the first channel signal and the second channel signal; and
   generating an ECG signal by performing a least mean square (LMS) filtering operation on the first channel signal to remove the motion artifact component,
   wherein the detecting includes subtracting from the first channel signal a signal obtained by dividing the second channel signal by the channel offset coefficient.

9. The method of claim 8, wherein the LMS filtering operation includes receiving an input signal and a request signal and outputting an output signal and an error signal, the first channel signal corresponding to the request signal, and the motion artifact component corresponding to the input signal.

10. The method of claim 9, wherein the generating the ECG signal comprises:
generating an internal coefficient by multiplying the error signal and the input signal;
generating the output signal by multiplying the input signal by the internal coefficient;
generating the error signal by performing subtraction on the request signal and the output signal; and
changing the internal coefficient to minimize the error signal.

11. The method of claim 10, wherein the internal coefficient is based on a step coefficient.

12. The method of claim 8, further comprising:
calculating a correlation between the first channel signal and the second channel signal; and
comparing the calculated correlation with a threshold correlation.

13. The method of claim 12, further comprising:
changing a position of at least one of the first and second channels if the calculated correlation does not exceed the threshold correlation.

14. A device comprising:
an electrocardiogram (ECG) sensor configured to,
calculate an offset coefficient based on a first signal from a first channel of a first measuring electrode and a second signal from a second channel of a second measuring electrode, the calculated offset coefficient indicating a difference between the first signal and the second signal,
determine a noise component based on the first signal, the second signal, and the calculated offset coefficient, and
perform a filtering operation such that the determined noise component is removed from the first signal,
wherein the sensor is configured to determine the noise component by dividing the second signal by the offset coefficient and subtracting a result of the dividing from the first signal.

15. The device of claim 14, wherein the calculated channel offset coefficient indicates a gain difference between the first and second signals.

16. The device of claim 14, wherein the filtering operation is a Least Mean Square (LMS) filtering operation.

17. The device of claim 14, wherein the sensor is configured to calculate a correlation between the first signal and the second signal, and output a request to change a position of the at least one of the first channel and the second channel based on whether the calculated correlation exceeds a threshold.

* * * * *